(12) United States Patent
Chigurupati et al.

(10) Patent No.: US 11,819,565 B2
(45) Date of Patent: Nov. 21, 2023

(54) METHODS AND COMPOSITIONS FOR INHIBITING FUNGAL GROWTH IN FOOD AND COSMETIC PRODUCTS

(71) Applicant: S&P Ingredient Development, LLC, Saint Louis Park, MN (US)

(72) Inventors: Sambasiva Rao Chigurupati, Omaha, NE (US); Sivaraj Annanmar, Omaha, NE (US); Ana Cristina Arciniega Castillo, Lincoln, NE (US)

(73) Assignee: S&P Ingredient Development, LLC, Saint Louis Park, MN (US)

( * ) Notice: Subject to any disclaimer, the term of this patent is extended or adjusted under 35 U.S.C. 154(b) by 0 days.

(21) Appl. No.: 17/950,733

(22) Filed: Sep. 22, 2022

(65) Prior Publication Data
US 2023/0090250 A1    Mar. 23, 2023

Related U.S. Application Data

(60) Provisional application No. 63/247,505, filed on Sep. 23, 2021.

(51) Int. Cl.
*A61K 36/9066* (2006.01)
*A61K 8/92* (2006.01)
*A61K 8/36* (2006.01)
*A01N 37/02* (2006.01)
*A01N 65/48* (2009.01)
*A61Q 19/00* (2006.01)
*A23L 3/3508* (2006.01)
*A23L 3/3472* (2006.01)
*A21D 15/08* (2006.01)
*A01P 3/00* (2006.01)

(52) U.S. Cl.
CPC .............. *A61K 8/922* (2013.01); *A01N 37/02* (2013.01); *A01N 65/48* (2013.01); *A01P 3/00* (2021.08); *A21D 15/08* (2013.01); *A23L 3/3472* (2013.01); *A23L 3/3508* (2013.01); *A61K 8/36* (2013.01); *A61Q 19/007* (2013.01); *A23V 2002/00* (2013.01); *A61K 2800/524* (2013.01)

(58) Field of Classification Search
None
See application file for complete search history.

(56) References Cited

U.S. PATENT DOCUMENTS

| 2009/0004308 A1 | 1/2009 | Frehner et al. |
| 2010/0172848 A1 | 7/2010 | Modak et al. |
| 2011/0028550 A1 | 2/2011 | Campano et al. |
| 2012/0251700 A1 | 10/2012 | Hofing et al. |
| 2016/0000094 A1 | 1/2016 | Modak et al. |

FOREIGN PATENT DOCUMENTS

| CN | 102885281 | 1/2013 |
| CN | 105341010 | 2/2016 |
| CN | 109700745 | 5/2019 |
| EP | 2014295 | 1/2009 |
| EP | 2179659 | 4/2010 |
| KR | 102010935 | 9/2019 |
| WO | WO 2016185488 | 11/2016 |

OTHER PUBLICATIONS

Apisariyakul et al. (1995) J. Ethnopharmacology 49: 163-169. (Year: 1995).*
Lind et al. (2005) Int. J. Food Microbiology 98: 157-165. (Year: 2005).*
Tallarida (2011) Genes and Cancer, 2(11): 1003-1008. (Year: 2011).*
International Search Report and Written Opinion in International Application No. PCT/US2022/076943, dated Jan. 17, 2023, 15 pages.
Gul et al., "Antimicrobial activity of turmeric extract and its potential use in food industry," J. Food Sci. Technol., Apr. 2015, 52(4):2272-2279.
Negi et al., "Antibacterial Activity of Turmeric Oil: A Byproduct from Curcumin Manufacture," J. Agric. Food Chem., 1999, 47:4297-4300.

* cited by examiner

*Primary Examiner* — Russell G Fiebig
(74) *Attorney, Agent, or Firm* — Fish & Richardson P.C.

(57) ABSTRACT

The present disclosure describes methods and compositions for inhibiting fungal growth in food and cosmetic products, as well as food and cosmetic products treated with antifungal compositions.

29 Claims, 2 Drawing Sheets

METHODS AND COMPOSITIONS FOR INHIBITING FUNGAL GROWTH IN FOOD AND COSMETIC PRODUCTS

CROSS REFERENCE TO RELATED APPLICATIONS

This application claims the benefit of priority under 35 U.S.C. § 119(e) to U.S. Application No. 63/247,505 filed on Sep. 23, 2021.

TECHNICAL FIELD

This disclosure generally relates to methods and compositions for inhibiting fungal/mold growth in food and cosmetic products.

BACKGROUND

Food spoilage due to the presence of microorganisms including fungi is a major issue for the food industry, leading to significant food waste and substantial economic losses for manufacturers and consumers. Fungal contamination can be encountered at various stages of the food chain (e.g., post-harvest, during processing or storage), and can lead to issues ranging from visual deterioration to noticeable odor, flavor, or texture changes. In some instances, fungal growth in food can negatively impact health due to, for example, mycotoxin production by some molds.

Similarly, cosmetic and beauty products can harbor microorganisms including fungi, which can cause products to become unpleasant and/or unsafe for consumers. Preservatives, including antimicrobial ingredients, can be added to product formulations to maintain the microbiological safety of the products by inhibiting the growth of and reducing the amount of microbial contaminants.

Currently, fungicides and chemical preservatives are used to inhibit fungal growth in food and cosmetic products, however, there is a demand by consumers for clean label products that are less processed. Therefore, new methods and compositions for inhibiting fungal growth in food and cosmetic products are needed.

SUMMARY

The present disclosure provides methods and compositions for inhibiting fungal growth in food and cosmetic compositions.

In one aspect, methods of inhibiting fungal growth in a food or cosmetic product are provided. Such methods typically include contacting the food or cosmetic product with an organic acid or salt and a spice oil or extract.

In some embodiments, the organic acid is a saturated aliphatic acids (e.g., formic acid, acetic acid, propionic acid), unsaturated aliphatic acids (e.g., sorbic acid), aromatic acids (e.g., benzoic acid), polycarboxylic acids (e.g., oxalic acid), hydroxyl acids (e.g., lactic acid), keto acids (e.g., pyruvic acid), and amino acids (e.g., glycine). In some embodiments, the organic acid is propionic acid.

In some embodiments, the spice oil or extract is from a spice selected from allicin, basil, bergamot, black pepper, cassia, catechin, chamomile, chitosan, cinnamon, citron, clary sage, clove, corlander, cumin, eucalyptus, fennel, frankincense, geranol, geranium, ginger, gingerol, grapefruit, honey, juniper berry, lavender, lemon, lemongrass, lime, marjoram, melissa, mengzong bamboo extract, orange, oregano, peppermint, petitgrain, rosemary, spearmint, St. John's wort, tangerine, tea tree, thyme, white mulberry, ylang. In some embodiments, the spice oil or extract is turmeric.

In some embodiments, the food product is selected from bakery products, meat and poultry products, dairy products, snacks, and pet foods. In some embodiments, the cosmetic product is selected from creams and lotions.

In some embodiments, the contacting step includes combining. In some embodiments, such methods further include combining the organic acid or salt and the spice oil or extract with a solvent to yield a composition, and contacting the food or cosmetic product with the composition.

In some embodiments, such methods further include packaging the food or cosmetic product.

In another aspect, anti-fungal compositions comprising, or consisting essentially of, or consisting of, an organic acid and a spice oil or extract.

In some embodiments, the organic acid is a saturated aliphatic acids (e.g., formic acid, acetic acid, propionic acid), unsaturated aliphatic acids (e.g., sorbic acid), aromatic acids (e.g., benzoic acid), polycarboxylic acids (e.g., oxalic acid), hydroxyl acids (e.g., lactic acid), keto acids (e.g., pyruvic acid), and amino acids (e.g., glycine). In some embodiments, the organic acid is propionic acid.

In some embodiments, the spice oil or extract is selected from allicin, basil, bergamot, black pepper, cassia, catechin, chamomile, chitosan, cinnamon, citron, clary sage, clove, corlander, cumin, eucalyptus, fennel, frankincense, geranol, geranium, ginger, gingerol, grapefruit, honey, juniper berry, lavender, lemon, lemongrass, lime, marjoram, Melissa, mengzong bamboo extract, orange, oregano, peppermint, petitgrain, rosemary, spearmint, St. John's wort, tangerine, tea tree, thyme, turmeric, white mulberry, ylang ylang. In some embodiments, the spice oil or extract is turmeric.

In some embodiments, the organic acid is a propionic acid and the spice oil or extract is turmeric. In some embodiments, the composition comprises a solvent.

In some embodiments, the composition is a food or cosmetic product.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Figure 1:
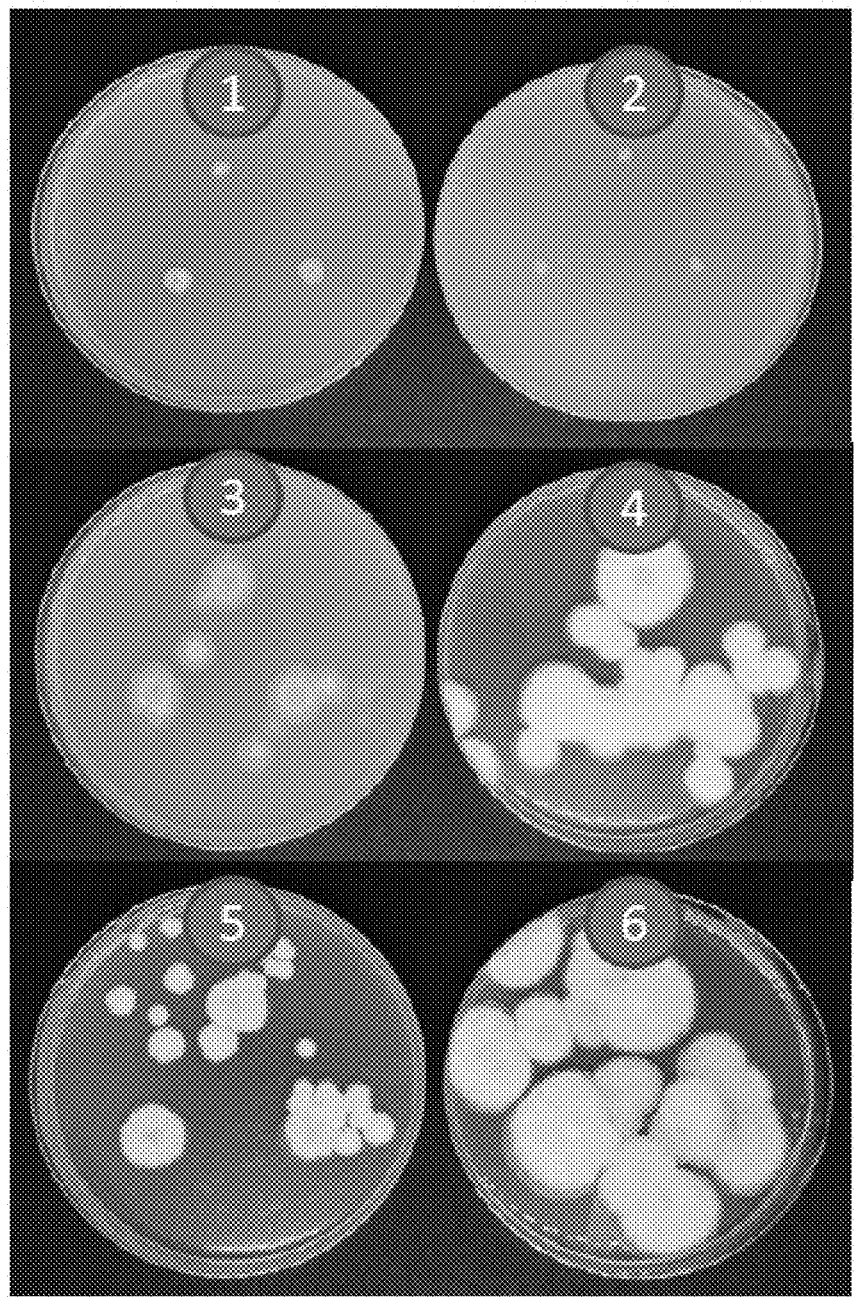
FIG. 1 shows the inhibition of *Aspergillus flavus* by the compositions described herein 5 days after inoculation.

The present disclosure describes an unexpected synergistic effect on inhibiting the growth of fungi in food and cosmetic products when an organic acid and a spice oil or extract are used in combination. In some instances, an organic acid is produced during the fermentation process (e.g., propionic acid can be produced when microorganisms are grown in the presence of dextrose or other sources such as wheat flour, tapioca, oats, or milk), referred to as natural organic acids or salts (e.g., natural calcium propionate); in other instances, an organic acid can be added exogenously, referred to as chemically derived organic acid (e.g., chemically derived calcium propionate).

In many food and cosmetic products, a level of about 0.5% w/w organic acid or salt thereof (e.g., calcium propionate) typically inhibits the growth of many fungi. The industry standard for establishing whether a compound inhibits growth of a microorganism is a 3-point inoculation of the compound into a culture plate followed by 5-days of incubation under suitable temperature and humidity conditions. After 5 days, the diameter and size of the fungal colonies indicates whether the compound is effective at inhibiting growth of the fungi.

The compositions and methods described herein can be used in virtually any food (e.g., human or animal) or cosmetic product that has a water activity (a w) that supports the growth of fungi or mold (e.g., food or cosmetic products having an a w of at least 0.60; at least 0.65, 0.70, 0.75, 0.80, 0.85, 0.90, or 0.95). For example, the compositions and methods described herein can be used in any number of food and cosmetic products including, without limitation, bakery and bread products, dairy products, pet foods and treats, meat and poultry products (e.g., meat snacks), plant-based foods (e.g., non-dairy products, plant-based burgers) and cosmetic products (e.g., creams and lotions). Suitable food and cosmetic products for use with the compositions and methods described herein can be fresh, refrigerated, frozen and/or partially dried.

In addition, a number of spice oils or extracts, including those from turmeric, have exhibited anti-fungal properties.

As demonstrated herein, the combination of an organic acid (e.g., propionic acid) or salt and a spice oil or extract (e.g., turmeric extract) shows surprising and synergistic fungal inhibitory properties. In some embodiments, the organic acid or salt and the spice oil or extract is combined directly with a food or cosmetic product to yield a treated food or cosmetic product. In other embodiments the organic acid or salt and the spice or extract are combined with a solvent to yield an anti-fungal composition, and the anti-fungal composition can be applied to a food or cosmetic product to yield a treated food or cosmetic product.

Organic Acids or Salts Thereof

Representative categories of organic acids are shown below, with representative examples of each.

1) Saturated aliphatic acids (e.g., formic acid, acetic acid)
2) Unsaturated aliphatic acids (e.g., sorbic acid)
3) Aromatic acids (e.g., benzoic acid)
4) Polycarboxylic acids (e.g., oxalic acid)
5) Hydroxy acids (e.g., lactic acid)
6) Keto acids (e.g., pyruvic acid)
7) Amino acids (e.g., glycine)

The following Table contains representative organic acids that can be used in the compositions described herein. Some of the organic acids listed below are generally recognized as safe (GRAS), have been used as anti-microbials and/or are considered as intermediates or products of sugar fermentation.

| Chemical | Common name | pKa1 | pKa2 | pKa3 |
|---|---|---|---|---|
| CH2O2 | formic acid | 3.75 | | |
| C2H2O3 | glyoxilic acid | 3.18 | | |
| C2H2O4 | oxalic acid | 1.27 | 4.26 | |
| C2H4O2 | acetic acid | 4.76 | | |
| C2H4O3 | giocolic acid | 3.83 | | |
| C3H4O2 | acrylic acid | 4.25 | | |
| C3H4O3 | pyruvic acid | 2.5 | | |
| C3H4O4 | malonic acid | 2.83 | 5.69 | |
| C3H6O2 | propanoic acid | 4.87 | | |
| C3H6O3 | hydroxypropanoic acid | 4.51 | | |
| C3H6O3 | lactic acid | 3.86 | | |
| C3H6O4 | glyceric acid | 3.52 | | |
| C4H4O4 | fumaric acid | 3.02 | 4.38 | |
| C4H4O4 | maleic acid | 1.93 | 6.58 | |
| C4H4O5 | oxaloacetic acid | 2.25 | 4.37 | 13.03 |
| C4H6O2 | crotonoic acid | 4.62 | | |
| C4H6O3 | acetoacetic acid | 3.58 | | |
| C4H6O3 | 2-oxobutanoic acid | 2.5 | | |
| C4H6O4 | methylmalonic acid | 3.07 | 5.76 | |
| C4H6O4 | succinic acid | 4.21 | 5.64 | |
| C4H6O5 | malic acid | 3.4 | 5.2 | |
| C4H6O6 | L-tartaric acid | 2.98 | 4.34 | |
| C4H6O6 | DL-tartaric acid | 3.03 | 4.37 | |
| C4H6O6 | meso-tartaric acid | 3.13 | 4.91 | |
| C4H6O8 | dihydroxytartaric acid | 1.92 | | |
| C4H8O2 | butanoic acid | 4.83 | | |
| C4H8O2 | isobutanoic acid | 4.86 | | |
| C4H8O3 | hydroxybutanoic acid | 3.65 | | |
| C5H6O4 | itaconic acid | 3.85 | 5.45 | |
| C5H6O4 | mesaconic acid | 3.09 | 4.75 | |
| C5H6O5 | oxoglutaric acid | 2.47 | 4.68 | |
| C5H8O4 | glutaric acid | 4.32 | 5.42 | |
| C5H8O4 | methylsuccinic acid | 4.13 | 5.64 | |
| C5H10O2 | valeric acid | 4.84 | | |
| C5H10O2 | isovaleric acid | 4.78 | | |
| C5H10O2 | pivalic acid | 5.03 | | |
| C6H6O | phenol | 9.99 | | |
| C6H6O6 | cis-aconitic acid | 1.95 | | |
| C6H6O6 | trans-aconitic acid | 2.8 | 4.46 | |
| C6H8O6 | ascorbic acid | 4.04 | 11.7 | |
| C6H8O7 | citric acid | 3.13 | 4.76 | 6.4 |
| C6H8O7 | isocitric acid | 3.29 | 4.71 | 6.4 |
| C6H10O4 | adipic acid | 4.41 | 5.41 | |
| C6H12O2 | caproic acid | 4.85 | | |
| C7H6O2 | benzoic acid | 4.2 | | |
| C7H6O3 | salicylic acid | 3.0 | 13.4 | |
| C7H6O4 | gentisic acid | 2.97 | | |
| C7H6O4 | protocatechuic acid | 4.48 | 8.83 | 12.6 |
| C7H6O5 | gallic acid | 4.41 | | |
| C7H12O2 | cyclohexanecarboxylic | 4.9 | | |
| C7H12O4 | pimelic acid | 4.48 | 5.42 | |
| C8H6O4 | phthalic acid | 2.95 | 5.4 | |
| C8H6O4 | isophthalic acid | 3.46 | 4.46 | |
| C8H6O4 | terephthalic acid | 3.51 | 4.82 | |
| C8H8O2 | phenylacetic acid | 4.31 | | |
| C8H8O2 | toluic acid | 3.91 | | |
| C8H8O2 | m-toluic acid | 4.27 | | |
| C8H8O2 | p-toluic acid | 4.37 | | |
| C8H8O3 | mandelic acid | 3.41 | | |
| C8H8O4 | homogentistic acid | 4.4 | | |
| C8H14O4 | suberic acid | 4.52 | 5.4 | |
| C8H16O2 | octanoic acid | 4.89 | | |
| C9H8O2 | cinnamic acid | 4.44 | | |
| C9H18O2 | nonanoic acid | 4.96 | | |
| C6H8O2 | sorbic acid | 4.76 | | |
| C4H4O4 | fumaric acid | 3.02 | | |
| C4H7O5 | malic acid | 3.40 | | |
| C4H6O6 | tartaric acid | 2.93 | | |
| C7H6O2 | benzoic acid | 4.19 | | |
| C76H52O46 | tannic acid | 6 | | |
| C16H18O9 | caffeotannic acid | ? | | |

Salts of these and other organic acids can include, without limitation, metal cations (e.g., alkali metal cations, alkaline earth metal cations, transition metal cations) such as potassium, lithium, sodium, calcium, zinc, magnesium or nonmetal cations such as ammonium.

The amount of organic acid in an anti-fungal composition or combined with a food or cosmetic product can range from about 0.01% up to about 5% w/w (e.g., about 0.05% to about 4.5%; about 0.1% to about 4.0%; about 0.5% to about 3.5%; about 1.0% to about 3.0%; about 1.5% to about 2.5%; about 1.75% to about 2.0%).

Spice Oil or Extract

Any number of spices can be used to produce oils or extracts for use in the compositions described herein. The following are considered GRAS and/or are used for medicinal purposes: allicin, basil, bergamot, black pepper, cassia, catechin, chamomile, chitosan, cinnamon, citron, clary sage, clove, corlander, cumin, eucalyptus, fennel, frankincense, geranol, geranium, ginger, gingerol, grapefruit, honey, juniper berry, lavender, lemon, lemongrass, lime, marjoram, melissa, mengzong bamboo extract, orange, oregano, peppermint, petitgrain, rosemary, spearmint, St. John's wort, tangerine, tea tree, thyme, turmeric, white mulberry, and ylang ylang.

One of the representative spices that has demonstrated synergy with an organic acid in the compositions described herein is turmeric. Turmeric (*Curcuma longa*) is a member of the Zingiberaceae family, and is used as a spice, food preservative and coloring material in many south Asian countries. Several turmeric-like compounds (e.g., sesquiterpenes and curcuminoids such as, without limitation, ar-turmerone, turmerone, and curlone) have been isolated from Turmeric and shown to have a variety of biological activities. Turmeric or a turmeric-like compound can be used in the compositions described herein in the form of an oil, an extract, a powder, or as a root alcohol.

Methods of obtaining oil or another extract from a spice, which typically takes the form of a plant or plant component, are known in the art. Methods typically include, without limitation, compression of the plant material (also referred to as plant biomass) using a shear force (e.g., generated by a screw press or a hydraulic press) to disrupt the hard coat of the seed and/or the cell walls of the plant tissue. Compression of the seed or other plant biomass, as well as frictional heat generated during the compression process (e.g., due to the shearing action), allows for oils or other phytochemicals that are harbored within the seed or other plant biomass to be liberated and collected. In addition to, or as an alternative to, a physical compression and/or shearing of plant biomass, extraction processes can use organic solvents (e.g., steam, super-critical carbon dioxide, hexane, butane, or isopropanol) to chemically extract the oils or desirable phytochemicals from plant biomass. If desired, chemical extraction steps can be followed by concentration steps (e.g., distillation) to remove any remaining organic solvents.

The amount of spice oil or extract can range from about 10 ppm up to about 10,000 ppm (e.g., about 50 ppm to about 5,000 ppm; about 50 ppm to about 500 ppm; about 100 ppm to about 4,000 ppm; about 100 ppm to about 2500 ppm; about 500 ppm to about 5,000 ppm; about 1000 ppm to about 5000 ppm; about 5000 ppm to about 10000 ppm; about 5000 ppm to about 7500 ppm; about 300 ppm to about 3000 ppm; about 500 ppm to about 2000 ppm).

In accordance with the present embodiments, there may be employed conventional molecular biology, microbiology, biochemical, and recombinant DNA techniques within the skill of the art. Such techniques are explained fully in the literature. The embodiments will be further described in the following examples, which do not limit the scope of the methods and compositions of matter described in the claims.

EXAMPLES

Example 1—Fungal Inhibition Experiments

Czapek Yeast Autolysate Agar (CYA Agar) was used to culture various species and strains of fungi in the presence or absence of a composition for inhibiting fungal growth. A 3-point inoculation was used and cultures were grown at 25° C.

Fungal samples recovered from commercially available products (e.g., pet foods) or obtained from NRRL Culture Collection were tested with various compositions for their ability to inhibit the different types of fungi. The following species and strains of fungi were used in the experiments described herein: *Aspergillus flavus, Aspergillus flavus* NRRL 1290, *Aspergillus parasiticus, Aspergillus parasiticus* NRRL 2999, *Aspergillus repens, Aspergillus oryzae* NRRL 3484, *Penicillium commune* NRRL 894, *Penicillium crustosum* FR 1809, *Penicillium expansum* NRRL 2304.

The following compositions were used in the experiments described herein:
(1) cultured dextrose (as a source of propionic acid or propionate equivalent to 0.5% w/w)+1000 ppm turmeric oil;
(2) cultured dextrose (as a source of propionic acid or propionate equivalent to 0.5% w/w)+3000 ppm turmeric oil;
(3) cultured dextrose alone (as a source of propionic acid or propionate);
(4) 1000 ppm turmeric oil alone;
(5) 3000 ppm turmeric oil alone; and
(6) no inhibitor added.

Figure 2:
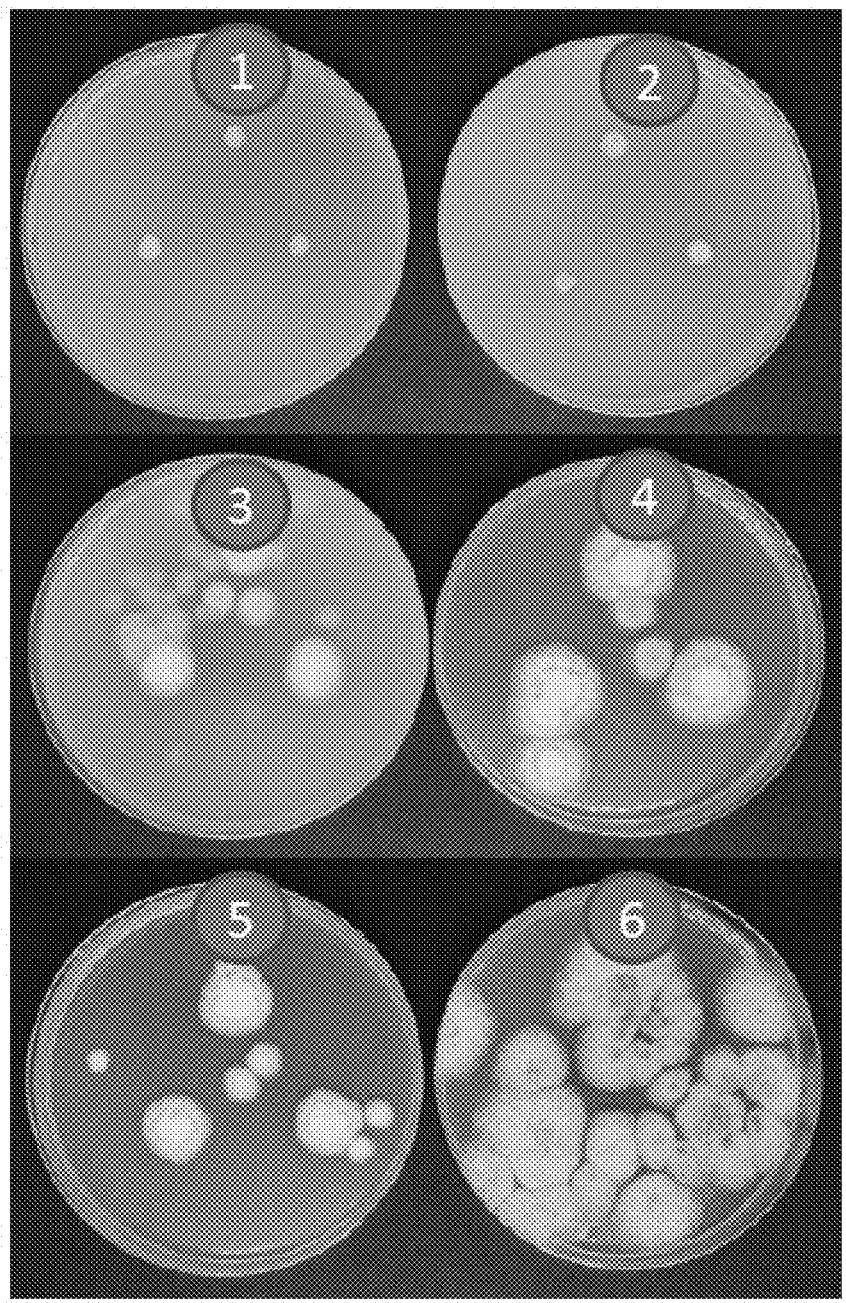
FIG. 2 shows the inhibition of *Aspergillus parasiticus* by the compositions described herein 5 days after inoculation.

FIG. 1 shows the extent of growth of *Aspergillus flavus* after 5 days in the presence of the above-indicated inhibitors (1)-(6), and FIG. 2 shows the extent of growth of *Aspergillus parasiticus* after 5 days in the presence of the above-indicated inhibitors (1)-(6). As demonstrated in culture dishes labeled as "1" and "2" in each of FIGS. 1 and 2, the presence of turmeric oil and cultured dextrose (as a source of propionic acid) significantly inhibited fungal growth.

Example 2—Fungal Inhibition Experiments in Bread

Methods
Media:
  standard bread recipe
Mold inhibitors:
  (1) no mold inhibitor;
  (2) cultured dextrose (0.5%)
  (3) cultured dextrose (1.0%)
  (4) turmeric oil (1000 ppm);
  (5) cultured dextrose (0.5%)+turmeric oil (250 ppm)
  (6) cultured dextrose (0.5%)+turmeric oil (500 ppm)
  (7) cultured dextrose (0.5%)+turmeric oil (1000 ppm)
  (8) acid blend (cultured dextrose+calcium lactate+vinegar)–1%;
  (9) acid blend (cultured dextrose+calcium lactate+vinegar)–1%+turmeric oil (500 ppm); and
  (10) acid blend (cultured dextrose+calcium lactate+vinegar)–0.5%+turmeric oil (500 ppm).

Observation
# of days to visual mold formation
qualitative flavor evaluation (for smell and taste) on the date of making
Formulations
The recipes shown in the following Table were used.

a number of compositions or methods are discussed, each and every combination and permutation of the compositions and the methods are specifically contemplated unless specifically indicated to the contrary. Likewise, any subset or combination of these is also specifically contemplated and disclosed.

| | No Mold Inhibitor | 0.5% Cultured Dextrose | 1% Cultured Dextrose | 1000 ppm Turmeric Oil | 0.50% Cultured Dextrose + 250 ppm Turmeric Oil | 0.50% Cultured Dextrose + 500 ppm Turmeric Oil | 0.50% Cultured Dextrose + 1000 ppm Turmeric Oil | 1% Acid Blend | 1% Acid Blend + 500 ppm Turmeric Oil | 0.5% Acid Blend + 500 ppm Turmeric Oil |
|---|---|---|---|---|---|---|---|---|---|---|
| Recipe | Gm | Gm | Gm | Gm | Gm | Gm | Gm | Gm | Gm | Gm |
| Bread flour | 100.00 | 100.00 | 100.00 | 100.00 | 100.00 | 100.00 | 100.00 | 100.00 | 100.00 | 100.00 |
| Water | 60.80 | 60.80 | 60.80 | 60.80 | 60.80 | 60.80 | 60.80 | 60.80 | 60.80 | 60.80 |
| Sugar | 3.10 | 3.10 | 3.10 | 3.10 | 3.10 | 3.10 | 3.10 | 3.10 | 3.10 | 3.10 |
| Instant yeast | 1.20 | 1.20 | 1.20 | 1.20 | 1.20 | 1.20 | 1.20 | 1.20 | 1.20 | 1.20 |
| dry milk | 9.50 | 9.50 | 9.50 | 9.50 | 9.50 | 9.50 | 9.50 | 9.50 | 9.50 | 9.50 |
| Butter | 5.80 | 5.80 | 5.80 | 5.80 | 5.80 | 5.80 | 5.80 | 5.80 | 5.80 | 5.80 |
| Salt | 2.60 | 2.60 | 2.60 | 2.60 | 2.60 | 2.60 | 2.60 | 2.60 | 2.60 | 2.60 |
| Cultured Dextrose | 0.00 | 0.50 | 1.00 | 0.00 | 0.50 | 0.50 | 0.50 | 0.33 | 0.33 | 0.17 |
| Calcium Lactate | 0.00 | 0.00 | 0.00 | 0.00 | 0.00 | 0.00 | 0.00 | 0.33 | 0.33 | 0.17 |
| Vinegar | 0.00 | 0.00 | 0.00 | 0.00 | 0.00 | 0.00 | 0.00 | 0.33 | 0.33 | 0.17 |
| Turmeric oil | 0.00 | 0.00 | 0.00 | 0.10 | 0.025 | 0.05 | 0.10 | 0.00 | 0.05 | 0.05 |
| Total | 183.00 | 183.50 | 184.00 | 183.10 | 183.53 | 183.55 | 183.60 | 183.99 | 183.60 | 183.60 |
| # Days to visual mold | 9 | 16 | 20 | 12 | 20 | 30 | 30 | 30 | 30 | 30 |
| Sensory (Taste & Flavor on day of making) | Acceptable | Acceptable | Acceptable | Acceptable | Acceptable | Acceptable | Acceptable | Acceptable | Acceptable | Acceptable |

From previous studies, the appearance of mold in the presence of 0.5% cultured dextrose was only 17 days.

CONCLUSIONS

The combination of fermented calcium salt of propionic acid and turmeric oil inhibits mold formation in bread for more days than in the absence of such a combination. Further, the combination of fermented calcium salt of propionic acid with calcium lactate, vinegar and turmeric oil inhibits mold formation in bread for more days than in the absence of such a combination, sometimes for significantly more days, than bread lacking such components.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and

What is claimed is:

1. An anti-fungal composition comprising about 0.5% w/w to about 3.5% w/w of an organic acid and about 50 ppm to about 500 ppm of turmeric.

2. The composition of claim 1, wherein the organic acid is a saturated aliphatic acids, unsaturated aliphatic acids, aromatic acids, polycarboxylic acids, hydroxyl acids, keto acids, amino acids, or combinations thereof.

3. The composition of claim 2, wherein the saturated aliphatic acid is selected from formic acid, acetic acid, and propionic acid.

4. The composition of claim 2, wherein the unsaturated aliphatic acid is sorbic.

5. The composition of claim 2, wherein the aromatic acid is benzoic acid.

6. The composition of claim 2, wherein the polycarboxylic acid is oxalic acid.

7. The composition of claim 2, wherein the hydroxyl acid is lactic acid.

8. The composition of claim 2, wherein the keto acid is pyruvic acid.

9. The composition of claim 2, wherein the amino acid is glycine.

10. The composition of claim 1, wherein the organic acid is propionic acid.

11. The composition of claim 1, wherein the organic acid is a blend of organic acids.

12. The composition of claim 11, wherein the blend of organic acids comprises propionic acid, lactic acid, and acetic acid.

13. The composition of claim 1, wherein the composition comprises a solvent.

14. A method of inhibiting fungal growth in a food or cosmetic product, comprising:

contacting the food or cosmetic product with an effective amount of the anti-fungal composition comprising about 0.5% w/w to about 3.5% w/w of an organic acid or salt thereof and about 50 ppm to about 500 ppm of turmeric.

15. The method of claim 14, wherein the organic acid is a saturated aliphatic acid, an unsaturated aliphatic acid, an aromatic acid, a polycarboxylic acid, a hydroxyl acid, a keto acid, an amino acid, or combinations thereof.

16. The method of claim 15, wherein the saturated aliphatic acid is selected from formic acid, acetic acid, and propionic acid.

17. The method of claim 15, wherein the unsaturated aliphatic acid is sorbic acid.

18. The method of claim 15, wherein the aromatic acid is benzoic acid.

19. The method of claim 15, wherein the polycarboxylic acid is oxalic acid.

20. The method of claim 15, wherein the hydroxyl acid is lactic acid.

21. The method of claim 15, wherein the keto acid is pyruvic acid.

22. The method of claim 15, wherein the amino acid is glycine.

23. The method of claim 14, wherein the organic acid is propionic acid.

24. The method of claim 14, wherein the organic acid is a blend of organic acids.

25. The method of claim 24, wherein the blend of organic acids comprises propionic acid, lactic acid, and acetic acid.

26. The method of claim 14, wherein the food product is selected from bakery products, meat and poultry products, dairy products, snacks, and pet foods.

27. The method of claim 14, wherein the cosmetic product is selected from creams and lotions.

28. The method of claim 14, further comprising combining the organic acid or salt and tumeric with a solvent to yield a composition, and contacting the food or cosmetic product with the composition.

29. The method of claim 14, further comprising packaging the food or cosmetic product.

* * * * *